United States Patent [19]

Ferrario

[11] Patent Number: 5,401,059
[45] Date of Patent: Mar. 28, 1995

[54] PROCESS AND UNIT FOR UNIVOCAL PAIRING OF DRUGS CORRESPONDING TO A PRESCRIBED TREATMENT WITH A GIVEN PATIENT

[75] Inventor: Angelo Ferrario, Busto Arsizio, Italy

[73] Assignee: Healtech S.A., Balzers, Liechtenstein

[21] Appl. No.: 920,292

[22] PCT Filed: Dec. 19, 1991

[86] PCT No.: PCT/EP91/02465

§ 371 Date: Aug. 14, 1992

§ 102(e) Date: Aug. 14, 1992

[87] PCT Pub. No.: WO92/10985

PCT Pub. Date: Sep. 7, 1992

[51] Int. Cl.[6] .............................................. B42D 15/00
[52] U.S. Cl. ......................................... 283/67; 283/70; 283/900; 221/2; 221/12
[58] Field of Search ........................... 283/67, 70, 900; 194/220, 221; 221/2, 12

[56] References Cited

U.S. PATENT DOCUMENTS

| | | | |
|---|---|---|---|
| 3,848,112 | 11/1974 | Weichselbaum et al. | 283/900 |
| 3,917,045 | 11/1975 | Williams | 194/4 |
| 4,121,574 | 10/1978 | Lester | 283/900 |
| 4,476,381 | 10/1984 | Rubin | 283/900 |
| 4,546,901 | 10/1985 | Buttarazzi | 221/10 |
| 4,730,849 | 3/1988 | Siegel | 283/70 |
| 4,847,764 | 7/1989 | Halvorson | 364/413.02 |
| 4,869,392 | 9/1989 | Moulding, Jr. et al. | 221/2 X |
| 4,953,745 | 9/1990 | Rowlett | 221/5 |
| 4,976,351 | 12/1990 | Mangini et al. | 283/900 X |
| 5,029,726 | 7/1991 | Pendill | 221/2 X |
| 5,071,168 | 12/1991 | Shamos | 283/900 X |
| 5,193,855 | 3/1993 | Shamos | 283/900 X |
| 5,292,029 | 3/1994 | Pearson | 221/2 |
| 5,329,459 | 7/1994 | Kaufman et al. | 221/2 X |

Primary Examiner—Paul A. Bell
Attorney, Agent, or Firm—Sixbey, Friedman, Leedom & Ferguson

[57] ABSTRACT

A process and apparatus are disclosed for pairing drugs corresponding to a prescribed treatment with a given patient including marking of arm bands or other identification devices with the patient's identification data, permanently attaching the identification device to the patient, retrieving a drug corresponding to the prescribed treatment and verifying its agreement with the drug administration data stored on the identification device, introducing the drug into a container which is previously marked with the patient identification data and drug administration data and closing the container. The process further includes moving the container to a drug delivery station at the patient location and verifying agreement of the data marked on the container with that stored on the identification device of the patient. Subsequently, the container is opened and agreement between the patient identification data marked on the identification device and the drug administration data marked on the container are verified with the drug subsequently being administered upon verification of the agreement.

9 Claims, 3 Drawing Sheets

PROCESS AND UNIT FOR UNIVOCAL PAIRING OF DRUGS CORRESPONDING TO A PRESCRIBED TREATMENT WITH A GIVEN PATIENT

The present invention relates to a process and a unit for univocal pairing of drugs corresponding to a prescribed treatment with a given patient.

The need is known of guaranteeing the safeness of operations leading to the administration of drugs to hospitalized patients.

Analysed as a whole, this problem imposes the need of automating, in a closed circle, the steps of assigning, preparing and administering drugs to a given patient.

Among these steps the most dangerous is obviously the administration of the drug. In fact, while any errors in the assignment and preparation can be remedied and reversed, this is obviously not true for the step of administration, wherein a safeness is required that is intrinsic and thus independent of the action of operators or of the patient himself.

Within this scope it is particularly important that the administration of the drug be preceded by a non-subjective verification with the patient's data so as to avoid any possible error derived from a possible exchange of the drugs destined for different patients.

It is also important, even though within certain tolerances to be determined and defined on a case by case basis, to observe the hours of administration.

The existence of staff shifts in the hospital, in the absence of an adequate automated support structure, causes these requirements to be observed only with difficulty, especially at night.

The object of the present invention is to accomplish a process and a unit which allow the avoidance of any possible error in administration, observing the set hours, and to execute the updating of the case sheets to confirm that administration has taken place.

According to the invention such objects are attained with a process for the univocal pairing of drugs corresponding to a given prescribed treatment with a given patient, characterized in that it provides for assignment of identification data to each individual patient, permanent association of said data to said patient through a support device that can be attached to the patient himself, prescription and writing into a case sheet of a treatment for said patient, withdrawal and recognizing of a drug corresponding to the prescribed treatment, introduction of the withdrawn drug into a container previously marked with identification data of the patient and of a drug administration to be performed, closure of said container, its transmission to a drug's delivery station, verification of the agreement between the data marked on the container and those of identification associated with the patient, opening of the container for extraction of the drug contained therein, verifying that it agrees with the treatment prescribed for the patient by reading said patient identification data on said support device and drug's identification data and comparing them one with the other and with the prescribed treatment and, in case of agreement, issuing a signal to enable the administration of the drug to the patient.

Preferably, the opening of the container takes place by removal of a part of it, which once administration has taken place is associated with the patient's case sheet to confirm that administration has taken place.

As an alternative, it may be provided that, once administration has taken place, a confirmation document is issued that can be associated with the patient's case sheet to confirm that administration has taken place.

For the execution of the abovementioned process a unit is provided which comprises essentially a machine for marking support devices for the patient's identification data, say, arm bands, a dolly machine for reading the patient's identification data, the recording of the prescribed treatment, the reading of the identification data of the drug to be administered and the issue of a signal to enable the administration of the drug itself, and a machine for the preparation and filling of a container with the prescribed drug.

The marking machine preferably comprises a magazine of the support devices for the patient's identification data and a transfer device that withdraws said support devices from said magazine to convey them in succession to a delivery station passing through means for marking and means for verifying the markings driven by a system for verifying and acquiring a patient's identification data, so as to univocally mark each individual device with the data related to a corresponding individual patient.

The marking machine is preferably connected to a remote admittance station for the exchange of information of an administrative and fiscal nature. The admittance station, if present, comprises a reader of an identification tag connected to a computer and/or a terminal for the temporary storage of the information read by the reader and to a central computer of the operational type. The functions of the admittance station can also be performed automatically on the part of the station for marking the support devices for the patient's identification data, which so as to facilitate the acquisition of the abovementioned data can be equipped with a special identification tag reader.

The dolly machine comprises preferably a reader of identification data capable of reading the data marked on the support devices attached to the patients and on the drug containers, a reader of data associated with the drug packages and a computer for recording the assigned treatments and for issuing an enabling signal in the case of the verification of the agreement between the drug to be administered and the prescribed treatment for a given patient, possible electronic-key device for opening the containers. The dolly machine may also be provided with means for issuing validation documents, possibly constituted by suitably-erased container parts, for their subsequent association with the patient's case sheet.

The machine for the preparation of the drug containers comprises preferably a magazine for containers and a container transfer device that withdraws containers from said magazine to convey them in succession to a delivery station passing through means for marking, means for verifying the markings, means for filling and means for closing driven by a system for verifying and acquiring a patient's identification data and a corresponding prescribed administration of drugs, so as to univocally mark each individual container with the data related to a corresponding individual patient and to a corresponding individual administration of drugs.

The features of the present invention shall be made more evident by an embodiment illustrated as a non-limiting example in the enclosed drawings, wherein.

Figure 1:
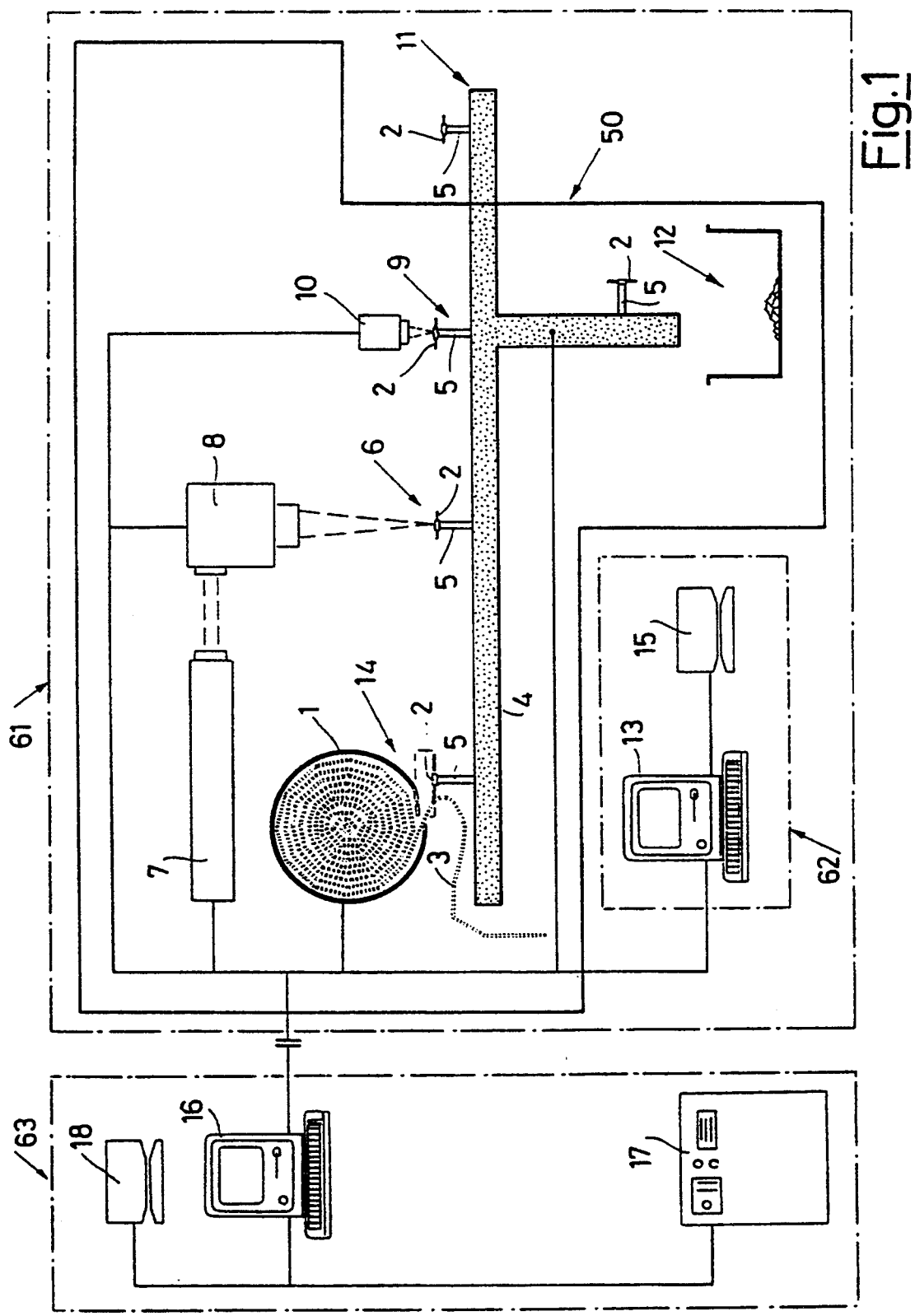
FIG. 1 illustrates a machine for marking arm band devices for the support of the patients' identification data.

With reference to FIG. 1, there is illustrated and indicated as a whole with 61 a machine for marking arm bands that can be attached to the body of patients, which, inside a machine casing 50 normally inaccessible from the outside, comprises a delivery station 14 wherein a magazine 1, for example in the shape of a cylindrical container, contains arm bands 2 arranged sequentially on a flexible support 3. Each arm band 2 is delivered on a corresponding support 5, which forms part of a transfer device 4 suitable for causing the passage of the abovementioned arm band 2 through stations for marking 6 and for verifying the markings 9.

The marking station 6 consists of a laser source 7 suitable for sending a modulated beam to a galvanometric head 8 in a position of displacing the laser beam in the plane perpendicular to the plane of the figure and tangential to the surface of the arm band 2 positioned at the marking station 6 to perform the arm band's indelible marking. Further details of the marking station are omitted, together with the indication of possible constructional variants thereof, referring for this to the detailed description contained in the U.S. patent application Ser. No. 07/962,577 filed Dec. 30, 1992, in the name of the same applicant.

The station for verifying the markings 9 comprises in turn an optical transducer 10 consisting of a television camera, of a set of diodes or of an optical fibre head for returning the signal to an optical transducer positioned at a distance.

The machine 61 also comprises delivery 11 and rejection 12 stations, to which the arm band 2 is sent in case at the station for verifying the markings 9 the agreement between the marking as executed and the desired marking has been verified or otherwise, respectively.

For the running of the operation of the delivery stations 14, of the stations for marking 6 and of the stations for verifying the markings 9 the machine 61 is equipped with a control and data acquisition system 62, which comprises a computer 13 of the personal type and a reader of an identification tag 15, through which it is possible to obtain the patient's indication data.

To the marking machine 61 there is also connected an admittance station 63, which comprises a computer 16 of the personal type connected to the computer 13 and to a central computer 17 of the operational type, as well as to a reader of an identification tag 18 by means of which it is possible to introduce into the central computer 17 and into the computers 16 and 13 the patient's data obtained at admittance.

Figure 2:
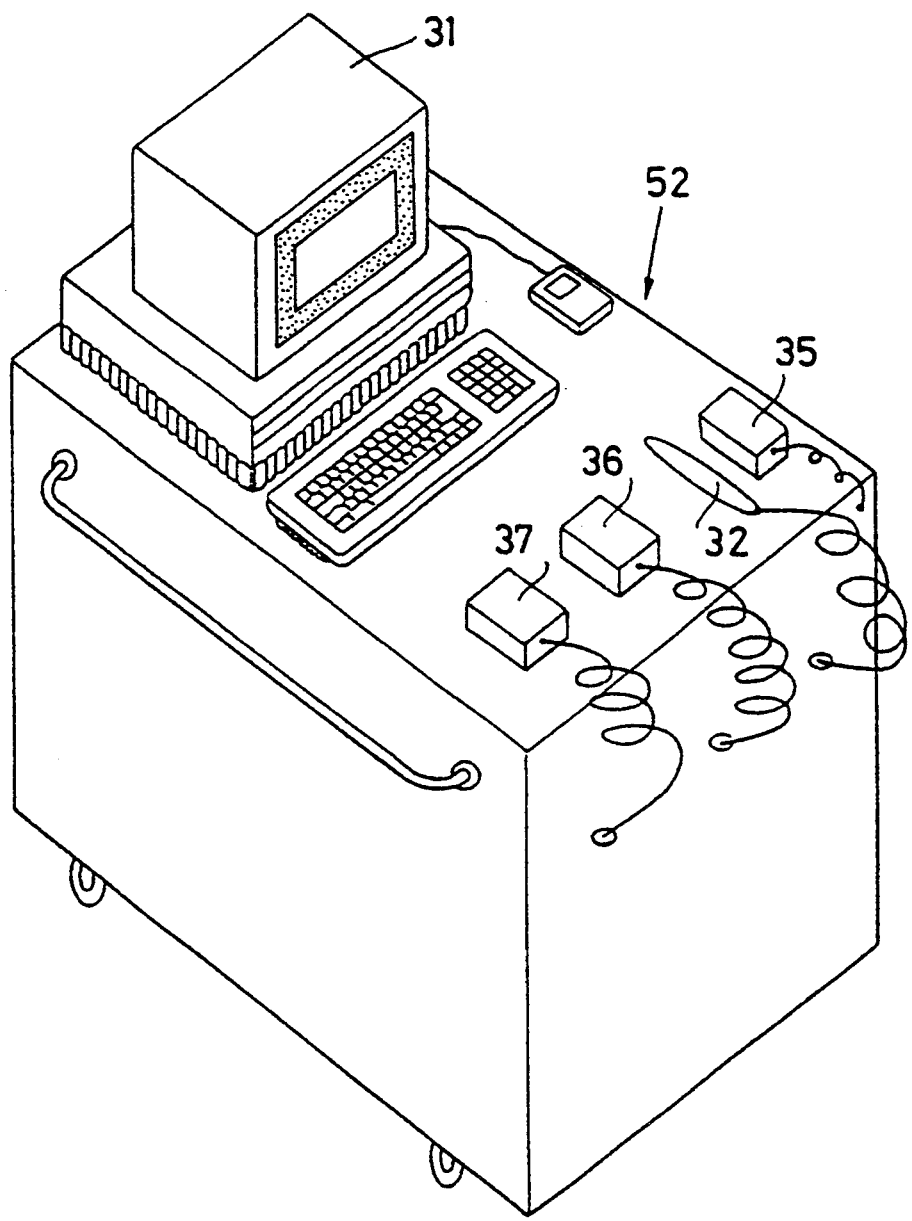
FIG. 2 illustrates a dolly machine for recording treatments and issuing signals to enable the administration of drugs.

With reference to FIG. 2, there is shown a dolly machine 52 which comprises a computer 31 of the personal type, a bar code reader 32, a reader 35 of identification data stored on the arm band 2 of the patient and/or on a drug container, an electronic-key device 36 for opening said drug containers and a device 37 for erasing labels associated with the abovementioned containers, possibly replaceable with a printer suitable for issuing documents to confirm that the administration of the drug has taken place.

Figure 3:
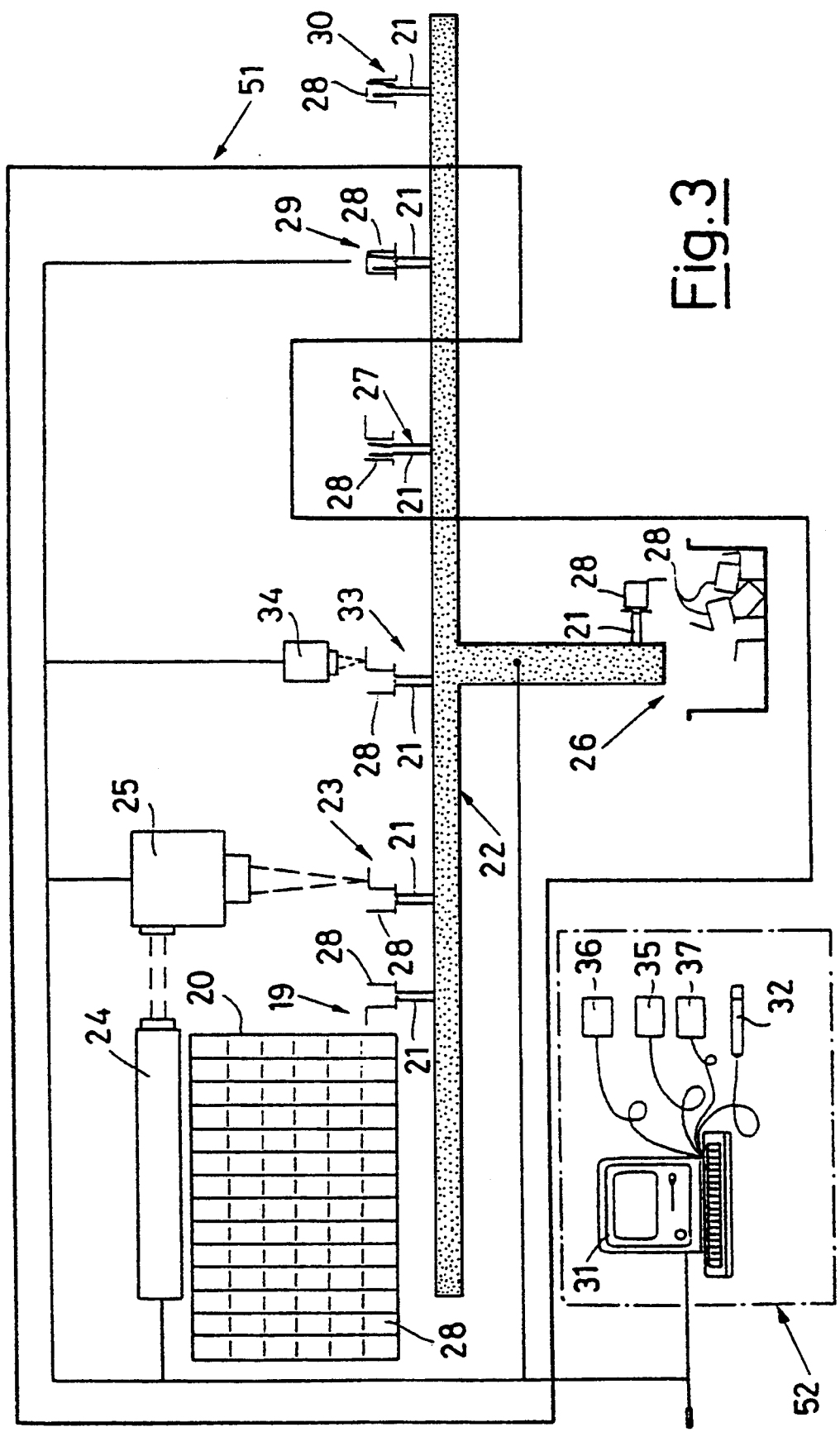
FIG. 3 illustrates a machine for the preparation of drug containers.

With reference to FIG. 3, a machine for the preparation of drug containers comprises, inside a machine casing 51 normally inaccessible from the outside, a container magazine 20, a delivery station 19 for the delivery of containers 28 from the magazine 20 to a support 21, which forms part of a transfer device 22 controlled by an external computer, which, for 10 example, can be the same computer 31 of the dolly machine 52 of FIG. 2.

It also comprises a writing and marking station 23 consisting of a laser source 24 which sends a modulated beam to a galvanometric head 25 for the deviation and the concentration of the laser beam, which performs the indelible marking of a label on the container 28 with the identification data of the patient and of the corresponding desired drug administration, as indicated by the computer 31.

In succession to the writing and marking station 23 there is a verification station 33, which through an optical transducer 34 executes the verification of the agreement of the data marked on the label with the original information related to the patient and to the treatment assigned to the patient himself, stored in the computer 31.

There is then a rejection station 26 suitable for receiving the containers for which the abovementioned agreement has not been verified.

Otherwise, there are in succession stations for filling 27, closing 29, delivering 30 the container 28 suitable for receiving the latter in the case wherein the abovementioned agreement has been verified.

At the filling station 27 the containers 28 are filled with drugs according to the treatment stored in the computer 31 after verifying the same by means of the bar code reader 32 connected to tile computer 31, which reads the bar codes usually present on drug packages.

The computer 31 also drives the operation of the transfer device 22, of the laser source 24 and of the galvanometric head 25 of the marking station 23, of the optical transducer 34 of the verification station 33 and of the means for closing associated with the station 29.

With reference to the mentioned figures, initially the patient shows lap at the admittance station 63 of FIG. 1, where he is identified by the appropriate staff, possibly by introducing his own identification tag into the reader 18. The corresponding identification data are stored in the central computer 17.

The marking machine 61 of FIG. 1 then delivers an arm band 2 destined to be attached to the patient for the identification of the patient himself on the occasion of every health-related event affecting him. In the absence of suitable equipment at the admittance station 63, the abovementioned operation can if necessary be carried out in an autonomous manner by the machine for marking and delivering the arm bands 61 of FIG. 1, possibly using for this purpose the reader 15 of identification tags in combination with the computer 31.

The appropriate staff applies the arm band to the patient, which from that moment on shall be identified only by means of said arm band on the occasion of every health-related event affecting him.

Once the patient has been hospitalized with the corresponding arm band applied, the medical staff, after identification of the same through the arm band, prescribes a suitable treatment, consisting in the administration of given drugs at certain hours. Such treatment is stored in the computer 31 of the dolly machine 52 of FIG. 2.

With reference to FIG. 3, the computer 31 of the abovementioned dolly machine, or other suitable computer in which information corresponding to a given patient has previously been introduced together with the corresponding drug treatment, drives the operation of the machine for the preparation of the drug containers.

In particular it drives the activation of the delivery station 19 for the delivery of a container 28 from the magazine 20 on a support 21. In succession the computer 31 operates the transfer of the container 28 to the marking station 23 for the compilation of the label, executed by means of a laser beam originating from the source 24 and driven by the galvanometric head 25.

The computer 31 then operates the passage of the container 28 through the verification station 33 where a verification is made on the agreement of the marking performed with the original information related to the treatment assigned to a given patient and stored in the same computer.

In the case where such agreement is not verified, the computer 31 operates the transfer of the container 28 to the rejection station 26. Otherwise, the container 28 passes to the filling station 27 to be filled with the drugs of the prescribed treatment, verified through the bar code reader 32 connected to the computer 31, and then in succession to the closing station 29 and to the withdrawal station 30.

For the administration of the drugs the dolly machine illustrated in FIG. 2 is used once again, on which the containers 28 are periodically loaded and on which the computer 31 is also present.

On the display of the computer 31 there appear in temporal succession the different drug treatments with the corresponding intervals of tolerance of administration. When a given treatment is actually administered the appropriate staff verifies with the reader 35 the agreement of the identification data (for example, a suitable code such as that of the prior patent application Ser. No. 07/962,577, filed Dec. 30, 1992) present on the arm band of the patient under treatment with those present on the label of the container 28. In the case wherein such agreement has been verified it proceeds with opening the container 28 and with removing the corresponding label by means of the electronic-key device 36 and with the extraction of the drug contained therein. After reading the patient's identification data and the drug's bar code by means of the readers 35 and 32, the computer 31 proceeds with verifying the agreement of said data and of the bar code with the treatment prescribed for that patient and then with the issue of a signal to enable the administration of the drug to the patient himself. Once administration has taken place, the label is erased and it is subsequently paired with the case sheet of the patient under treatment. It should be noted that no administration takes place when the agreement between the information on the arm band 2 and that on the label of the container 28, as well as with the stored treatment, has not been verified.

It is claimed:

1. A process for univocal pairing of drugs corresponding to a prescribed treatment with a given patient at a patient location, said process comprising the following steps:
   a) providing identification data for the patient;
   b) writing said identification data on a data storing device and on a support device which is then attached to the patient;
   c) prescribing a patient treatment with drug administration and writing treatment and drug administration data on the storing device;
   d) picking up a drug corresponding to the prescribed treatment and verifying its agreement with the drug administration data on the storing device;
   e) introducing the drug into a container previously marked with the patient identification data and the drug administration data and closing the container;
   f) moving the container to a drug delivery station at the patient location;
   g) verifying agreement of the data marked on the container with those stored on the storing device;
   h) opening the container and extracting the drug therefrom;
   i) reading the patient identification data marked on the support device and the drug administration data marked on the container to verify agreement of the drug with the prescribed patient treatment; and
   j) in case of agreement, issuing a signal to enable administration of the drug to the patient wherein the container is opened by removing a container part and connecting the container part to a patient case sheet to confirm that the drug administration has been carried out.

2. The process of claim 1, wherein said patient identification data consists of a personal code of the patient.

3. An apparatus assembly for univocal pairing of drugs corresponding to a prescribed treatment with a given patient at a patient location, comprising:
   a) a first machine for marking support devices for connection to the patient with patient identification data;
   b) a second machine for marking containers with said patient identification data and with drug administration data, filling the containers with drugs corresponding to said drug administration data and closing filled containers;
   c) a dolly machine movable between the patient location and said second machine for moving the filled container and including a reading means for reading data on said support devices connected to the patient and said containers, processing means for comparing said data to verify agreement therebetween and for causing a signal issuing device to issue
   a drug administration enabling signal when agreement is verified, and means responsive to said signal for opening said containers.

4. The apparatus assembly of claim 3, wherein said first machine, comprises a magazine for said support devices, a marking station for providing markings on said support devices, a marking verifying station for checking agreement of said markings with patient identification data, a delivery station for said support devices and transfer means for moving said support devices from said magazine to said delivery station passing through said marking and verifying station.

5. The apparatus assembly of claim 4, wherein said marking machine is connected to a remote admittance station comprising a data reader connected to local and central computer systems.

6. The apparatus assembly of claim 3, wherein said second machine comprises a container magazine, a marking station for providing markings on the containers, a verifying station for checking agreement of said markings with patient identification data and drug administration data, a filling station for filling said containers with drugs corresponding to said drug administration data, a closing station for closing filled containers, a delivery station for delivering filled and closed containers and transfer means for moving the containers from said magazine to said delivery station passing through said marking, verifying, filling and closing stations.

7. The apparatus assembly of claim 3, wherein said dolly machine further comprises an electronic-key controlled device for opening the drug containers for administration of drugs contained therein.

8. The apparatus assembly of claim 3, wherein said dolly machine further comprises an erasing data on device for erasing labels associated with the drug containers.

9. The apparatus assembly of claim 3, wherein said dolly machine further comprises a printer for issuing a confirmation document of the drug administration.

* * * * *